United States Patent [19]
Dhara et al.

[11] Patent Number: 5,269,769
[45] Date of Patent: Dec. 14, 1993

[54] CATHETER GUIDE SYSTEM FOR MANAGEMENT OF DIFFICULT UPPER AIRWAY MANEUVERS

[75] Inventors: Sasanka S. Dhara; Wen H. Yong, both of Singapore, Singapore

[73] Assignee: Biosensors International PTE Ltd., Singapore, Singapore

[21] Appl. No.: 894,736

[22] Filed: Jun. 4, 1992

[51] Int. Cl.$^5$ .............................................. A61M 5/00
[52] U.S. Cl. ............................ 604/264; 128/207.14
[58] Field of Search .............. 604/264, 247, 239, 275, 604/280, 283, 284; 128/207.14

[56] References Cited

U.S. PATENT DOCUMENTS

| | | | |
|---|---|---|---|
| 4,681,100 | 7/1987 | Brychta et al. | 128/207.14 X |
| 4,815,459 | 3/1989 | Beran | 128/207.14 |
| 5,060,646 | 10/1991 | Page | 128/207.14 |
| 5,065,754 | 11/1991 | Jensen | 128/207.14 X |

OTHER PUBLICATIONS

Akinyemi, O. O., John, A., "A Complication of Guided Blind Intubation", *Anesthesia*, (1974), 29: 733–735.
Akinyemi, O. O., "Complication of Guided Blind Endotracheal Intubation", *Anesthesia*, (1979), 34: 590–592.
Barriot, P., Rious, B., "Retrograde Technique for Tracheal Intubation in Trauma Patients", *Critical Care Medicine*, (1988), 16: 712–713.
Bedger, R. C., Chang, J. L., "A Jet-Stylet Endotracheal Catheter for Difficult Airway Management", *Anesthesiology*, (1987). 66:221–223.
Benumof, J. L., "Management of the Difficult Adult Airway", *Anesthesiology*, (1991), 75: 1087–1110.
Borland, L. M., Swan, D. M., Leff, S., "Difficult Pediatric Entrotracheal Intubation: A New Approach to the retrograde technique", *Anesthesiology*, (1981), 55:577–578.
Bourke, D., Levesque, P. R., "Modification of Retrograde Guide for Endotracheal Intubation", *Anesthesia and Analgesia*, (1974), 53: 1013–1014.
Carlson, C. A., Perkins, H. M., "Solving a Difficult Intubation", *Anesthesiology*, (1986), 64: 537.

Dhara, S. S., "Guided Blind Endotracheal Intubation", *Anesthesia*, (1980), 35: 81.
Dhara, S. S., "A Catheter Guide System in Management of Difficult Upper Airway (Its Uses in Anesthesia and Intensive Care)", *7th ASEAN Congress of Anesthesiologist*, (1991), Kuala Lumpur, Malaysia, pp. 1–9.
Findlay, C. W., Gissen, A. J., "A Guided Nasotracheal Method for Insertion of an Endotracheal Tube", *Anesthesia and Analgesia*, (1961), 40: 640–642.
Freund, P. R., Rooke, A., Schwid, H., "Retrograde Intubation with a Modified Eschman Stylet", *Anesth. Analg*, (1988), 67: 605–606.
Green, C. G., "Improved Technique for Fiberoptic Intubation", *Anesthesiology*, (1986), 65: 835.
Harmer, M., Vaughan, R., "Guided Blind Oral Intubation", *Anesthesia*, (1980) 35: 921.
King, H. K., "Translaryngeal Guided Intubation Using a Sheath Stylet", *Anesthesiology*, (1985), 63: 567.
King, H. K., Wang, L. F., Khan, A. K., Wooten, D. J., "Translaryngeal Guided Intubation for Difficult Intubation", *Critical Care Medicine*, (1985), 16:869–871.
Latto, I. P., Rosen, M., "Management of Difficult Intubation In: Difficulties in Tracheal Intubation", (1985), London, Bailliere Tindall, pp. 122–126.
Moorthy S. S., Dierdorf, S. F., "An Unusual Difficulty in Fiberoptic Intubation", *Anesthesiology*, (1985), 63: 229.

(List continued on next page.)

*Primary Examiner*—John D. Yasko
*Attorney, Agent, or Firm*—Trask, Britt & Rossa

[57] ABSTRACT

A catheter guide system for management of difficult upper airway intubation includes a multilumen catheter having one large central lumen and two smaller lumens defined in the sidewall of the catheter. A tubular adaptor is usable with the catheter when disposed over its proximal end to isolate the proximal end lumen outlets from each other for communication thereof with fluid sources such as oxygen and anesthetic and with monitoring devices.

14 Claims, 4 Drawing Sheets

OTHER PUBLICATIONS

Nunn, Utting & Brown, "General Anesthesia", (1989), Butterworths, pp. 512-539.

Powell, W. F., Odzil, T., "A Translaryngeal Guide for Tracheal Intubation", *Anesthesia and Analgesia*, (1967), 46: 231-234.

Robert, K. W., "New Use for Swan-Ganz Introducer Wire": *Anesthesia and Analgesia*, (1981), 60: 67.

Scurr, C., "A Complication of Guided Blind Intubation", *Anesthesia*, 30: 411-412.

Tahir, A. H., "A Simple Manoeuvre to Aid the Passage of a Nasotracheal Tube Into the Oropharynx", (1970), *British Journal Anesthesia* 42: 631-632.

Waters, D. J., "Guided Blind Retrograde Intubation: For patients with Deformities of the Upper Airway", *Anesthesia*, 18:2 158-162.

CATHETER GUIDE SYSTEM FOR MANAGEMENT OF DIFFICULT UPPER AIRWAY MANEUVERS

BACKGROUND OF THE INVENTION

1. Field of the Invention

The present invention relates generally to tracheal intubation, and more specifically to an airway catheter guide system for retrograde intubation.

2. State of the Art

Failure to maintain a patent airway for more than a few minutes can result in brain damage or death. Tracheal intubation is an essential procedure for maintaining a patent airway in patients receiving general anaesthesia for certain kinds of operations, for assisting ventilation in patients with ventilatory insufficiency, and to protect the lungs where protective reflexes of the larynx are inadequate. A categorized list of indications for this procedures is set forth as follows:

Upper airway obstruction
  Foreign body
  Tumour
  Infection
  Laryngospasm
  Bilateral vocal cord paralysis
Airway control
  Epiglottitis
  Surgical field adoidance during anaesthesia
  General anaesthesia in other than supine position
  Prolonged anaesthesia
Prevention of aspiration
  Bulbar neuromuscular disease
  Coma
  Stroke
  Drug overdose
  General anaesthesia for patient with full stomach
  General anaesthesia for parturient
  General anaesthesia for prolonged surgical procedures
Inability to clear tracheobronchial secretions
  Neuromuscular diseases:
    Quadriplegia
    Myasthenia gravis
    Ascending polyneuritis
  Flail chest and lung contusion
  Pneumonia
  Respiratory failure
Need for mechanical ventilation
  Respiratory failure
  Paralysis
    Neuromuscular disease
    Muscular relaxation for surgery
  Central nervous system trauma
  Anaesthesia for intrathoracic surgery There are numerous ways to intubate a trachea, the choice of which depends on the preference of the anesthesiologist. For a patient with a normal airway, blind nasotracheal intubation in a spontaneously breathing awake patient has a good chance of success, yet the risk of causing upper airway bleeding may cause the anesthesiologist to turn to direct laryngoscopy. In any case, there are times when anesthesiologists are faced with management of difficult airway during intubation procedures.

Difficulty in intubation may be caused by one or more of the following: congenital facial and upper airway deformities, maxillofacial and airway trauma, airway tumors and abscesses, anatomical deformities in the nasopharyngeal or oropharyngeal region, the requirement for cervical spine immobility, fibrosis of the face and neck (burns or radiation), surgically induced deformities, and some systemic diseases. Attempts to push a endotracheal tube blindly through obstacles in the upper airway may result in excessive trauma and bleeding, possibly leading to severe glottic spasm or asphyxia. Bleeding prevents clear visualization of vocal cords, leading to further complication in the intubation process. Arthritis of temporomandibular joint or trismus limits the exposure of the patient's mouth, thus prevents the use of conventional direct laryngoscopy.

The management of the difficult airway may follow the algorithm shown in FIG. 1 of the drawings. Awake tracheal intubation is generally preferred. For an awake patient, the natural airway is better maintained and the muscle tone is enough to maintain the airway structure, which eases intubation.

Special techniques and instruments are required in managing the difficult airway. Since its first introduction in 1960, retrograde intubation, also referred as translaryngeal guided intubation, has been successfully used on patients with ankylosis of the jaw, cervical arthritis, tumors of the mouth and recently on patients with severe maxillofacial trauma. It is also an effective technique for securing the airway at an accident scene or in prehospital care of trauma patients, and for unexpectedly difficult intubation in operating theatres. The technique has a high success rate, is easy to learn and requires little practice. However, while apparatus for retrograde intubation is simple, it is not readily available in hospitals as there is no standardized equipment or procedure.

A planned retrograde intubation may be performed under local anaesthesia using light sedation and translaryngeal anaesthesia. A wide bore needle such as a 16 G Tuohy needle is used to puncture the cricothyroid membrane percutaneously towards cephalad (FIG. 2a). Air aspiration into a syringe filled with sterile water is used to confirm the position of the needle within the lumen of the larynx. Once the position is located, the syringe is removed and a guide (vascular guide wire or epidural catheter) is inserted through the needle (FIG. 2b) and threaded between the vocal cords into the pharynx. When an epidural catheter is used, it may coil up in the pharynx. The catheter may be spat out or retrieved from the patient's mouth by using Magill forceps (FIG. 2c). The needle is then withdrawn and the guide is secured at puncture site using a hemostat. For oral intubation, the endotracheal tube can be placed directly over the guide or a suction catheter can be passed over the original guide to provide a larger and stiffer guide for the tracheal tube (FIG. 2d). Once the top of the endotracheal tube reaches the cricothyroid membrane (FIG. 2e), the guide is released at the puncture site and is removed from above. The endotracheal tube is further advanced into the final position in the trachea (FIG. 2f).

If nasal intubation is intended, a soft plastic suction catheter is inserted through the nose into the pharynx and brought out through the mouth (FIG. 3). The tip of the retrograde catheter and the proximal end of the suction catheter are tied together with suture and the retrograde catheter is pulled back through the pharynx and out of the nose. In another approach employed by S. S. Dhara, one of the inventors of the present invention, a length is cut from the tip of the suction catheter and the epidural catheter is fed through the lumen of the suction catheter until it protrudes from the nasal end. The suction catheter is then completely retrieved to bring the epidural catheter out from the nose. The tracheal tube is then inserted over the retrograde catheter and into the larynx. The rest of the procedure is similar to that for orotracheal intubation.

Several variations of the apparatus and technique used in guided retrograde intubation have been employed in the prior art. These variations were designed and used to solve complications encountered during retrograde intubation. However, such prior art apparatus and technique all possess one or more deficiencies.

A relatively large and stiff endotracheal tube threaded over a soft catheter guide or a thin flexible fibreoptic endoscope in fibreoptic aided intubation may be diverted into the esophagus (FIG. 4), resulting in esophageal intubation. Long flexible tip retrograde guide wires such as the Seldinger type intravascular guide wire or teflon coated Swan-Ganz introducer wire provides better stiffness and control over an epidural catheter. However, discrepancy between the outer diameter of the guide wire and the inner diameter of the endotracheal tube may cause the endotracheal tube to move round the guide, causing the endotracheal tube to hang up on the glottis (FIG. 5), epiglottis and arytenoid cartilages.

Various techniques have been used for reproducible and successful guiding of the endotracheal tube into the trachea, including use of a stiffer retrograde guide, and by reduction of the discrepancy in diameters b enlarging the external diameter of the retrograde guide using an anterograde guide over it in a one-stop Seldinger type technique. Frozen suction catheter warmed-up plastic sheath stylet, cut gum elastic Eschmann stylet (FIG. 6), and fibreoptic bronchoscopes have been used. The type of anterograde guide used currently depends very much on the convenience and availability of the devices, and preference of individual anesthesiologist.

All of the foregoing anterograde guides have to stop at the point of puncture at the cricothyroid membrane. When the retrograde guide is completely withdrawn for further insertion of the endotracheal tube, the tube may dislodge from the laryngeal inlet, resulting in esophageal intubation. One of the modifications to prevent the dislodgement of endotracheal tube is to pass the guide through the "Murphy eye" of the tracheal tube (FIG. 7) to allow for an additional 1 cm of the endotracheal tube within the trachea prior to removal of the guide. In another approach, a gum elastic bougie (FIG. 8) was inserted through the tracheal tube and used as an anchor for further insertion of the tracheal tube. The disadvantage of this method is the inability to fit the gum elastic bougie through the tracheal tube and the anterograde catheter.

Breathholding and respiratory (inspiratory) obstruction may occur during the insertion of an epidural catheter and endotracheal tube. Sometimes, oxygen administration is necessary during intubation. Extra doses of topical local anaesthetic may be needed during the procedure to suppress the reflex arising from upper airway. An anterograde guide which allows continuous ventilation, measurement of airway pressure and respiratory gases, and application of local anaesthetic without disrupting the insertion of endotracheal tube would be extremely useful in such situations.

To the inventors' knowledge, there is only one kit marketed for retrograde intubation (Cook, Australia). Cook's retrograde guide wire is rather thick and stiff. The anterograde guide is a long, narrow single lumen tapered nylon tubing. The step or gradual tapering of the anterograde guide is a very important factor for guiding such as in intravascular catheterization where the Seldinger wire, dilator and sheath make a smooth cone. The discrepancy in diameters between the anterograde guide and the endotracheal tube leaves a large gap causing the endotracheal tube to be "caught" in the glottic inlet.

Little emphasis has been placed in the designing of an anterograde guide with regards to appropriate stiffness and diameter. The anterograde guide should be flexible enough to follow the retrograde guide along the curvatures of the upper airway. At the same time, it must have adequate stiffness for its primary function as an anterograde guide so as to avoid the endotracheal tube straying into the oesophagus.

Ventilation, monitoring of airway pressure or sampling of respiratory gases may be required during or immediately after the procedure of intubation. The "jet stylet" described by Bedger, et al. (1987) provides ventilation through a narrow long catheter which is inadequate for more than a few minutes. Measurement of airway pressure is very important while this mode of ventilation is employed, yet prior art apparatus makes no provision to facilitate such monitoring.

Administration of local anaesthetic into the upper respiratory tract during the procedure may be needed, yet again prior art devices do not readily accommodate such a requirement.

Anchoring of the anterograde catheter to prevent dislodgement of the endotracheal tube when the hold of the retrograde guide is being discontinued and the endotracheal tube is being negotiated through the laryngeal inlet is very important. However, there is currently no easily reproducible manoeuvre available to achieve this.

SUMMARY OF THE INVENTION

The airway catheter guide system of the present invention overcomes the above-enumerated deficiencies of prior art apparatus and procedures and provides an easily employed means and method for facilitating the management of difficult airways during retrograde intubation.

The catheter guide system of the present invention comprises a multilumen airway catheter and a cooperating adaptor which renders the catheter suitable for high frequency jet ventilation during intubation, with simultaneous measurement of airway pressure or respiratory gas sampling. The airway catheter is employed as an anterograde catheter in retrograde intubation procedures to guide the insertion of an endotracheal tube and prevent dislodgement from the larynx while the retrograde guide is withdrawn.

The catheter itself includes three separate channels or lumens, one large and two smaller ones. The large channel is of irregular cross section and extends the entire length of the catheter, and includes two lateral openings immediately adjacent the distal end or tip. The smaller channels are located in the wall of the catheter and extend from slightly different levels at the proximal end of the catheter and terminate on diametrically opposite sides of the catheter approximately 1.5 cm and 3 cm, respectively from the distal end.

The three channel openings at the proximal end of the catheter can be mutually isolated for purposes of jet ventilation by utilization of the airway adaptor of the present invention When placed on the proximal end of the catheter, the airway adaptor includes three internal seals or O-rings to separate the annulus between the catheter and the adaptor into three chambers, each communicating with a catheter lumen and having a port extending through the wall of the adaptor. Each port terminates in a luer lock fitting for connection to a ventilation gas source, monitoring device, or syringes to instill local anesthetic into the respiratory tract.

The tapered proximal end of the catheter provides an easily connectable and disconnectable resilient, frictional interface with the adaptor via the O-rings. The tapered end also easily fits into the cut end of a 14 FG suction catheter if required to increase the effective length of the catheter used as a guide for an endotracheal tube during intubation.

DETAILED DESCRIPTION OF THE PREFERRED EMBODIMENT

Figure 1:
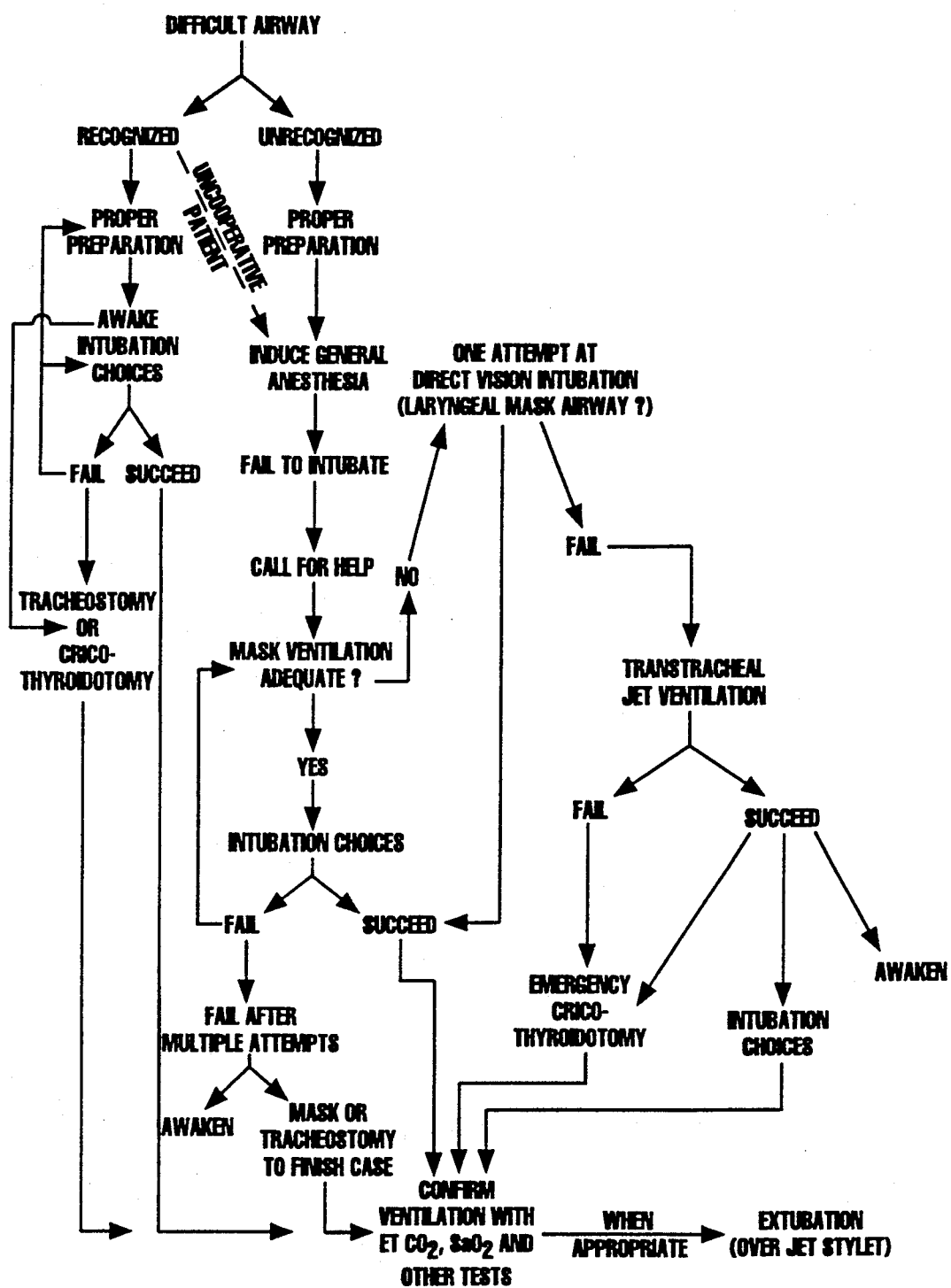
FIG. 1 is a graphic depiction of an algorithm for management of a difficult airway.
Figure 2A:
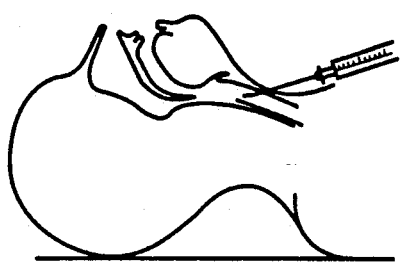
FIGS. 2a-2f schematically depicts the steps in a retrograde intubation performed without the apparatus of the present invention.
Figure 2D:
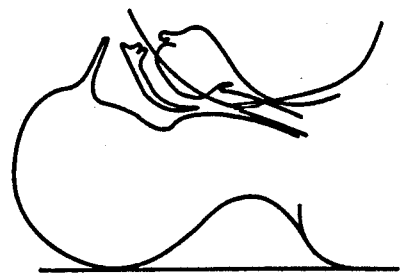
Figure 2B:
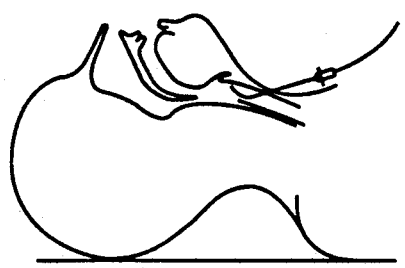
Figure 2E:
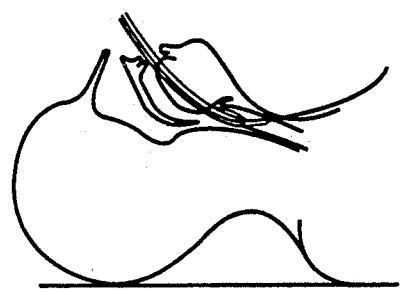
Figure 2C:
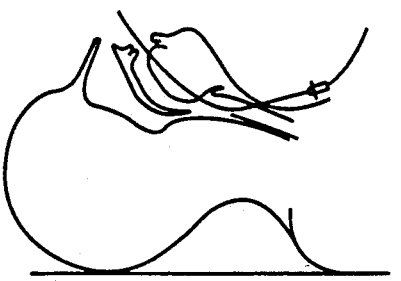
Figure 2F:
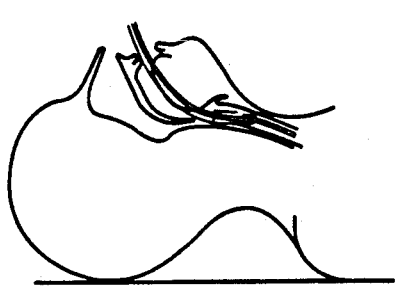
Figure 3:
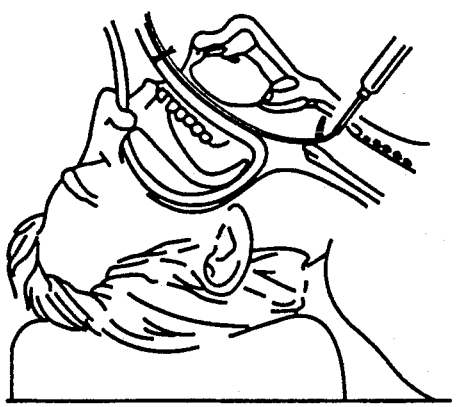
FIG. 3 schematically depicts apparatus employed in a nasal intubation.
Figure 4:
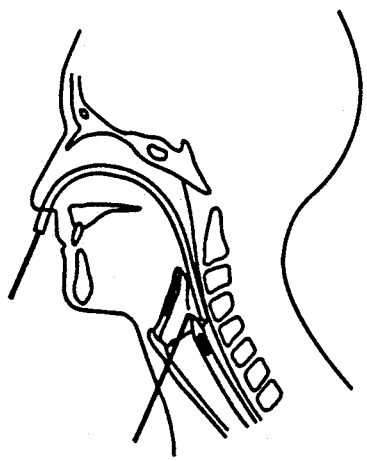
FIG. 4 schematically depicts the undesirable phenomenon of esophageal intubation.
Figure 5:
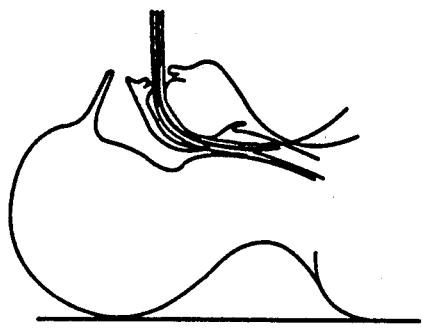
FIG. 5 schematically depicts the hang up of an endotracheal tube on the glottis.
Figure 6:
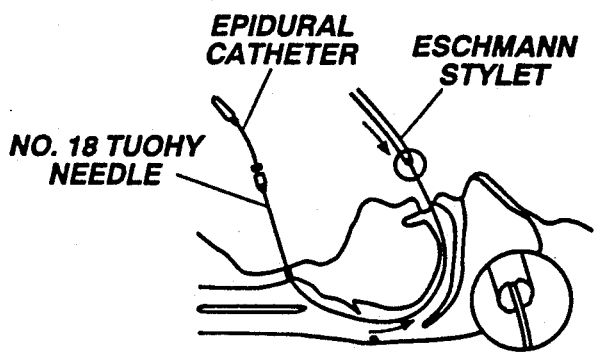
FIG. 6 schematically depicts a prior art method guiding an endotracheal tube.
Figure 7:
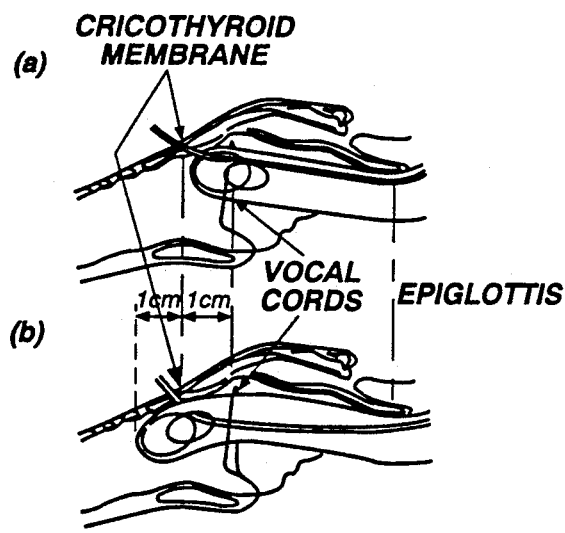
FIGS. 7 and 8 schematically depict prior art techniques for preventing dislodgement of the endotracheal tube.
Figure 8:
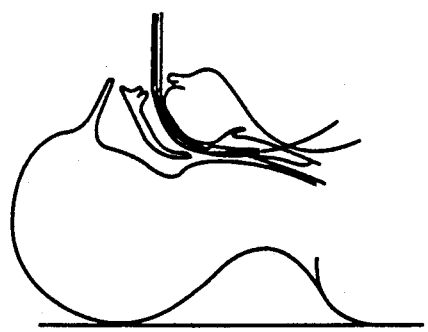
Figure 9:
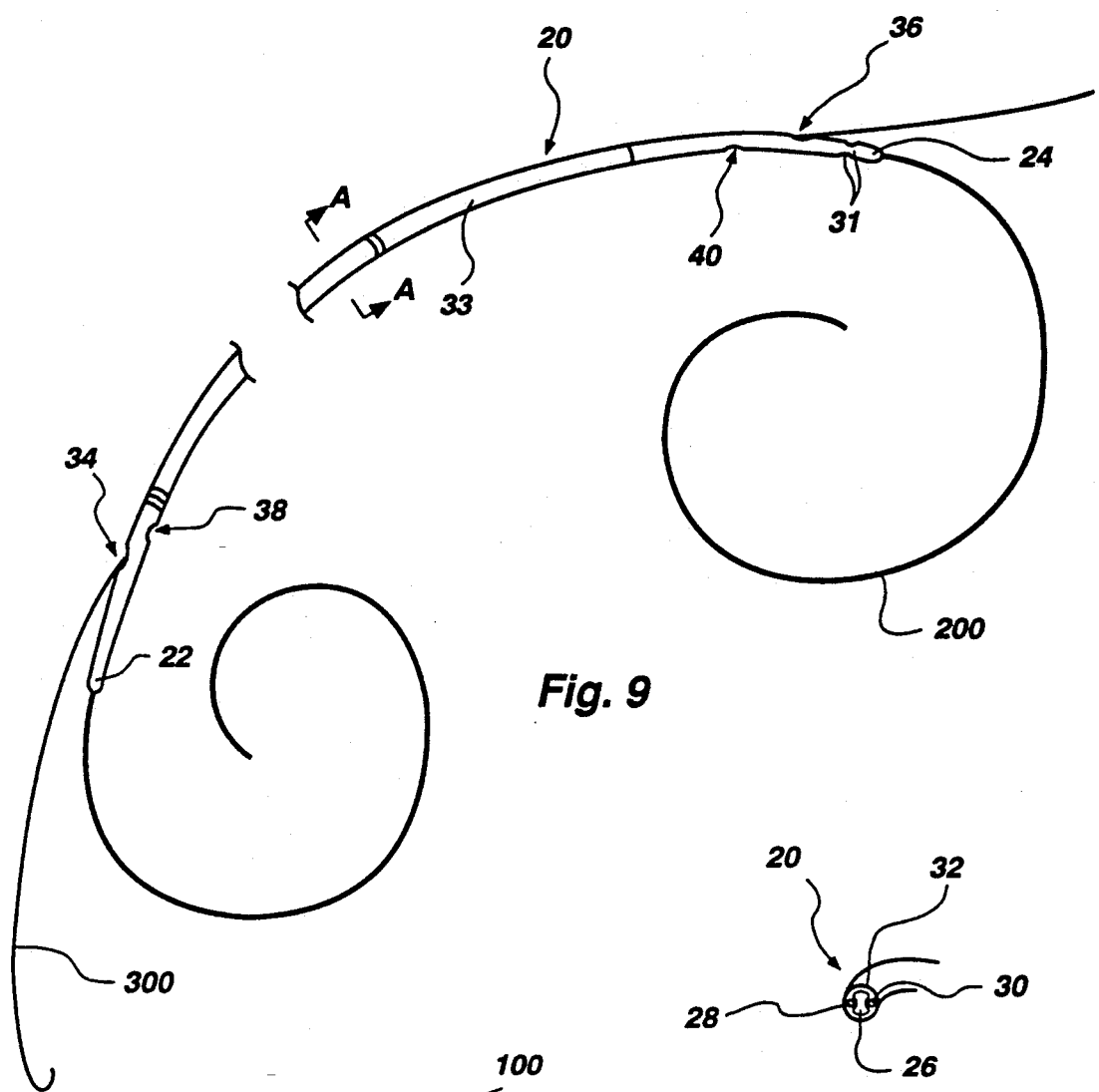
FIG. 9 is an elevation of an airway catheter in accordance with the present invention.
Figure 9A:
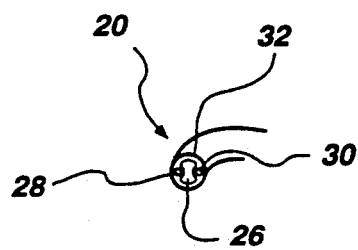
FIG. 9a is a cross-sectional view of the interior of the catheter of FIG. 9 taken along lines A—A.
Figure 10:
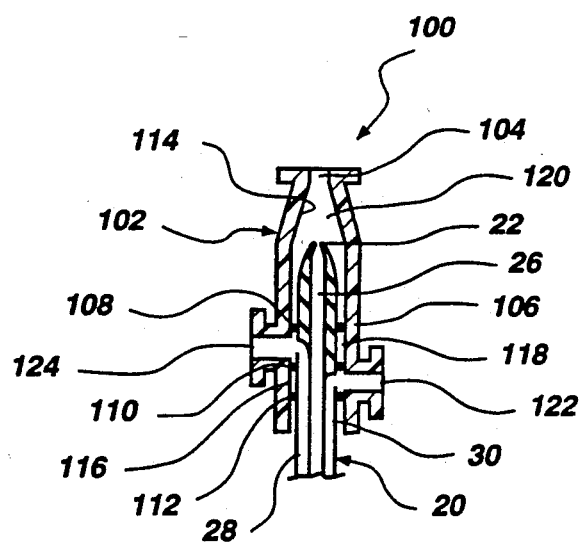
FIG. 10 is a schematic sectional view of the airway adaptor in accordance with the present invention applied to the proximal end of the airway catheter of FIG. 9.

Referring to FIGS. 9, 9a and 10 of the drawings, the airway catheter guide system of the present invention comprises multilumen airway catheter 20 as depicted in FIG. 9, which may be employed alone or in combination with airway adaptor 100 in a retrograde intubation procedure.

Airway catheter 20 comprises a one-piece 35 cm long extrusion of a radiopaque elastomeric material such as medical grade polyvinyl chloride (PVC) having a Shore A durometer harness of 80-100, and a stiffness of 20-50 MPa as measured with a Tinius Olsen stiffness tester. It is gradually tapered both at proximal end 22 and at distal end or tip 24, and is preferably graduated on its exterior as shown in FIG. 9 at 10, 15, 20 and 25 cm from distal end 24.

Catheter 20 defines a maximum external diameter of 4.75 mm, gradually tapering to 3.5 mm at both ends and includes three longitudinal channels or lumens 26, 28 and 30. As may be seen by reference to FIG. 9a, large central channel 26 is of irregular cross-sectional shape due to the presence of smaller side channels 28 and 30 which are formed in the wall 32 of catheter 20 as it is being extruded during the manufacturing process. The wall thickness between the central channel 26 and the outer diameter of the catheter is 0.6-0.7 mm, and channels 28 and 30 are each of 1.2 mm interior diameter.

Large central channel 26 extends throughout the entire length of catheter 20 between outlets or apertures through proximal end 22 and distal end 24, and is intersected near (about 5 mm from) distal end 24 by 1 mm side exits or passages 31. Side channel 28 extends from an outlet or aperture 34 about 3.8 cm from the proximal end 22 of catheter 20 on its exterior surface 33 to an aperture 36 approximately 1.5 cm from the distal end or tip 24. Side channel 30 extends from an aperture 38 about 4.8 cm from proximal end 22 to an aperture 40 approximately 3.0 cm from the distal end or tip 24. Apertures 34, 36, 38 and 40 are of approximately 4 mm in width and are produced by removing wall material from the catheter to expose the underlying channel, the border of catheter material surrounding each aperture being generally scalloped in configuration. The apertures at each end of one of the two side channels are marked, such as by a dot on the catheter exterior, for ease of identification.

Referring to FIG. 10 in the drawings, airway adaptor 100 is shown placed over the proximal end 22 of catheter 20. Adaptor 100 includes a generally cylindrical clear plastic housing 102 comprised of clear acrylic or polycarbonate having a port 104 luer lock ventilation connector at one end and a barrel 106 in which are disposed three axially separated (by about 12 mm) rubber O-rings or seals 108, 110, 112. The interior diameter of barrel 106 is about 5.5 mm, and the inner diameter defined by O-rings 108-112 in an uncompressed state is about 4.5 mm. While not specifically shown in FIG. 10 due to its schematic nature, the wall of barrel 106 is sufficiently thick to accommodate annular grooves on the interior thereof in which O-rings 108, 110 and 112 are disposed and maintained after each is compressed and inserted into barrel 106, the expansion of each O-ring after insertion in barrel 106 ensuring proper seating in its corresponding groove.

When proximal end 22 of catheter 20 is inserted into barrel 106 of adaptor 100, O-rings 108, 110 and 112 are compressed by the exterior 33 of catheter 20 and divide the annular space between the inner wall 114 of barrel 106 and the exterior surface 33 of catheter 20 into three chambers 116, 118 and 120, each of which is in communication with a port extending through the wall of barrel 106. Port 122 opens into chamber 116, port 124 opens into chamber 118 and port 104 opens into chamber 120. Each port terminates at a luer lock fitting for easy connection to gas sources or monitoring equipment. Due to the previously noted spacing of apertures 34 and 38 from the proximal end 22 of catheter 20 and cooperative spacing of the O-rings 108-112 and ports 122 and 124, aperture (also termed side lumen) 34 opens into adaptor chamber 116 while aperture 38 opens into adaptor chamber 118. The proximal end of large channel 26 opens into chamber 120. Thus, when adaptor 100 is placed over the proximal end 22 of the catheter 20, a manifold is created which may be used to employ fluid sources (such as oxygen, air, anesthetic) and monitoring devices with airway catheter 20 during an intubation procedure.

It should also be noted that tapered proximal end 22 of catheter 20 also fits into the cut end of a suction catheter such as 14 FG PVC tubing to form a firm connection when needed to increase the length of catheter guide needed during intubation.

A brief description of a retrograde intubation procedure employing the present invention will be described. For a planned retrograde intubation, the patient may be premedicated with mild sedative. In the operating room, routine monitoring such as ECG, NIBP and Pulse Oximetry is used. An intravenous line is established and the patient is further sedated using incremental doses of Fentanyl and Midazolam if necessary. The mouth and nostril are sprayed with 4% Lignocaine. The patient is positioned supine with comfortable extension of the neck. The front of the neck is cleaned and draped and a skin wheal is raised on the skin over the area of cricothyroid membrane with 1-2 ml of 1% Lignocaine.

The needle is advanced through the cricothyroid membrane, the syringe is changed and 2-3 ml of 4% Lignocaine is injected into the cavity of the larynx after confirmation of the position of the needle by aspiration of a free flow of air.

The larynx is stabilized by holding with the thumb and the index finger, the cricothyroid membrane is identified and a 16G I/V Cannula is used to puncture the cricothyroid membrane at a 45° angle with tip pointing cephalad. The needle stylet is withdrawn. Gentle sedation on the water-filled syringe connected to the back of the cannula will confirm the presence of the tip inside the airway by the free flow of air bubbles. To establish the retrograde guide through the mouth, 1-2 cm insertion of the cannula is adequate whereas for nasal placement, it may be necessary to push the cannula all the way in. A J-tipped vascular guide wire 200, 70 cm in length and 0.8 mm in diameter, is passed through the lumen of the cannula and is advanced till it comes out from the desired route. In case the guide wire does not come out through the intended nasal route, in patients who can open their mouths, a small, soft plastic 8 or 10 FG suction catheter may be passed through the nose and be brought out through the mouth. A length of guide wire can be simply loaded into the lumen of the suction catheter and be retrieved from the nasal passage upon withdrawal of the suction catheter from the nose. This obviates tying the guide wire and suction catheter together as done in the prior art, a requirement which wastes time and may be traumatic to the nasal mucous membrane and turbinates. The lower end of the retrograde guide wire 200 outside the skin must be secured with a pair of forceps.

Once the retrograde guide wire 200 is established through the desired route, the upper end of it is inserted through the large channel 26 of the well lubricated anterograde catheter 20 of the present invention. The catheter 20, used as a guide, is pushed gently till it reaches just behind the puncture site on the cricothyroid membrane, which presence is easily observed by the I/V cannula being pushed out and a tug on the guide wire outside the skin on manipulation of catheter 20. If any resistance is felt during the negotiation, a rotating movement of the catheter 20 over the guide wire 200 with simultaneous gentle push will advance the catheter 20. The side port or aperture 36 of the channel 28 terminating closest to the catheter tip 24 is identified and another guide wire 300 similar to the first one is passed through it. As the tip of the second guide wire 300 reaches lower trachea or touches the carina, a cough subdued by the local anaesthetic is produced confirming its presence in the depth of the trachea. The retrograde guide wire 200 is now withdrawn from the top end as the catheter 20 is pushed down over the second guide wire 300 into the depth of the trachea. A 14 FG plastic suction catheter without the flanged end is now connected to the tapered catheter upper end 22 over the second guide wire 300 to extend the length of the catheter guide. A well lubricated armoured tube or a PVC endotracheal tube softened in warm water can now be easily passed over the airway catheter 20, suction catheter and guide wire into the trachea. In case of PVC tubes, it is useful to disconnect the 15 mm endotracheal connector which could hinder the progress of the extension catheter (suction catheter) through the endotracheal tube.

The process of passing the endotracheal tube through the nose and through the larynx may be distressing to the patient despite sedation and local anaesthetic. A sleep does of intravenous induction agent, e.g., Thiopentone or Propofol, before the endotracheal tube is negotiated just into the trachea may be required. Once in the trachea, the catheter 20 along with the suction catheter and second guide wire 300 is withdrawn from the endotracheal tube. During the procedure, sedation combined with partial airway obstruction may result in a drop in oxygen saturation in these patients. Once the airway catheter 20 is in the trachea, oxygen may be delivered either by insufflation or by jet ventilation through the central channel 26. The ventilation can be continued throughout the placement of the endotracheal tube till the catheter 20 is withdrawn and the endotracheal tube connected to the breathing system. The catheter 20 may be used for suction while being withdrawn from the endotracheal tube.

The roles of the anterograde airway catheter guide system of the present invention can be summarized as follows. The interposition of the airway catheter 20 over the retrograde wire 200 provides smooth transition of an endotracheal tube into the trachea. The matching diametrical consistency between the anterograde airway catheter 20 and the endotracheal tube allows the endotracheal tube to follow the catheter as a guide without taking a loop of the airway catheter 20 with it, which would dislodge the airway catheter 20 from the laryngeal inlet.

The streamlined configuration of the airway catheter 20 allows the tip 24 of the catheter 20 to follow the retrograde guide wire without getting "caught" along it. Catheter 20 is flexible enough to negotiate various curvatures, yet is firm enough to be a guide for the endotracheal tube.

The 35 cm length of catheter 20 comes in handy for manipulation. The tapered proximal end 22 of the catheter 20 allows quick and firm attachment of a suction catheter, hence providing a temporary extension of the catheter 20. The extended length is very useful in certain procedures involving endotracheal intubation.

The side opening or aperture 34 of channel 28 at 1.5 cm away from the distal end or tip 24 is in line with the inlet of the larynx when the tip 24 of the airway catheter 20 stops at the puncture site behind the cricothyroid membrane. A J-tipped guide wire 300 when placed through channel 28 will go straight into the depth of the trachea without difficulty and serves as an anchor for further insertion of the catheter 20 after the retrograde guide wire 200 is withdrawn.

The central channel 26 of catheter 20 may be used for jet ventilation and airway pressure measurement even when a suction catheter is attached as an extension. The procedure could be carried out once the airway catheter 20 is inside the trachea and the retrograde guide wire 200 is withdrawn. Ventilation is necessary if oxygen desaturation occurs during the insertion of the endotracheal tube. Having the situation under control, the insertion of the endotracheal tube may be proceeded.

Any of the channels of the airway catheter 20 can be used for instilling local anesthetics at any stage of maneuver. They can also be used to apply suction while catheter 20 is being withdrawn from the endotracheal tube.

The capability of this multi-lumen airway catheter to be a guide for endotracheal intubation, and at the same time be a conduit for high frequency jet ventilation, opens up many possibilities for its use, such as a guide for difficult re-intubation, changeover of endotracheal tubes from orotracheal to nasotracheal route or vice versa, microlaryngeal operations including microlaryngeal laser surgery, elective high frequency jet ventilation, upper or lower tracheal resection, or trial or extubation.

The catheter guide system of the present invention has been used for all the above purposes and was found to be a very useful piece of equipment in operating theatres and intensive care areas. A package of airway catheter 20, airway adaptor 100 and a J-tipped guide wire together with other retrograde intubation equipment would be handy for difficult intubation even for patients with maxillofacial trauma at the scene of an accident.

A smaller catheter in accordance with the present invention would be useful for infants and smaller children for the similar purposes.

While the invention has been described in terms of an illustrated embodiment, it is not so limited, and those of ordinary skill in the art will readily observe and appreciate that many additions, deletions and modifications to the invention as disclosed herein may be effected without departure from the scope of the following claims.

What is claimed is:

1. A catheter guide system for management of difficult upper airway intubation, comprising:
   a catheter tapered at both proximal and distal ends and including a large central lumen and two smaller lumens defined in the sidewall of said catheter; and
   a tubular adaptor sized to fit over one end of said catheter and to define a manifold therewith for isolated communication of each of said lumens with the exterior of said adaptor.

2. The catheter guide system of claim 1, wherein said multilumen catheter is gradually tapered at both ends.

3. The catheter guide system of claim 1, wherein said first smaller lumen opens onto the exterior of said catheter about 1.5 cm from said distal end.

4. The catheter guide system of claim 1, wherein said second smaller lumen opens onto the exterior of said catheter about 3.0 cm from said distal end.

5. The catheter guide system of claim 1, wherein the distal end of said large lumen is intersected by at least one lateral passage leading to the side of said catheter.

6. The catheter guide system of claim 2, further including a tubular adaptor sized to fit over said proximal end of said catheter.

7. The catheter guide system of claim 1, wherein said tubular adaptor includes a plurality of O-rings transversely disposed on the interior thereof and spaced so as to define three chambers between the interior of said adaptor and the exterior of said catheter when said adaptor is disposed over said catheter, the outlet of the proximal end of each of said lumens communicating with a different one of said chambers.

8. The catheter guide system of claim 7, further including a port communicating each of said chambers with the exterior of said adaptor.

9. The catheter guide system of claim 8, wherein each of said ports includes a luer lock connector.

10. The catheter guide system of claim 7, wherein the uncompressed inner diameter of said O-rings is less than the outer diameter of said catheter away from said proximal end taper, whereby said O-rings are compressed when said adaptor is disposed over said proximal end.

11. The catheter guide system of claim 1, wherein said large central lumen extends substantially the entire length of said catheter.

12. The catheter guide system of claim 11; wherein one of said smaller lumens terminates at an aperture about 1.5 cm from said proximal end of said catheter, and the other of said smaller lumens terminates at an aperture about 3.0 cm from said proximal end of said catheter.

13. The catheter guide system of claim 1, wherein said catheter comprises a one-piece medical grade PVC extrusion having a Shore A durometer hardness of 80–100 and a stiffness of 20–50 MPa as measured with a Tinius Olsen stiffness tester.

14. The catheter guide system of claim 1, wherein said catheter has a maximum outer diameter of about 4.75 mm and a diameter at its ends of about 3.5 mm.

* * * * *

UNITED STATES PATENT AND TRADEMARK OFFICE
CERTIFICATE OF CORRECTION

PATENT NO. : 5,269,769
DATED : 12/14/93
INVENTOR(S) : Dhara et al

It is certified that error appears in the above-identified patent and that said Letters Patent is hereby corrected as shown below:

In Column 1, line 19, change "procedures" to --procedure--;

In Column 2, line 4, change "a" to --an--;

In Column 2, line 12, change "prevents" to --preventing--;

In Column 3, line 30, change "b" to --by--;

In Column 4, line 68, after "invention" insert a period;

In Column 5, line 20, change "depicts" to --depict--;

In Column 5, line 37, change the period to a semicolon;

In Column 8, line 15, change "does" to --dose--;

In Column 9, line 32 delete "the"; and

In Column 10, line 36, change the semicolon to a comma.

Signed and Sealed this

Eleventh Day of October, 1994

*Attest:*

BRUCE LEHMAN

*Attesting Officer*  *Commissioner of Patents and Trademarks*